United States Patent
Declerck et al.

(10) Patent No.: US 9,171,366 B2
(45) Date of Patent: Oct. 27, 2015

(54) METHOD FOR LOCALIZATION OF AN EPILEPTIC FOCUS IN NEUROIMAGING

(71) Applicants: Jerome Declerck, Oxford (GB); Kinda Anna Saddi, Oxford (GB)

(72) Inventors: Jerome Declerck, Oxford (GB); Kinda Anna Saddi, Oxford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 12 days.

(21) Appl. No.: 14/208,315

(22) Filed: Mar. 13, 2014

(65) Prior Publication Data

US 2014/0270438 A1  Sep. 18, 2014

(30) Foreign Application Priority Data

Mar. 13, 2013  (GB) .................................. 1304446.6

(51) Int. Cl.
| | |
|---|---|
| *G06K 9/00* | (2006.01) |
| *G06T 7/00* | (2006.01) |
| *G06T 7/20* | (2006.01) |
| *A61B 6/03* | (2006.01) |
| *A61B 6/00* | (2006.01) |

(52) U.S. Cl.
CPC ............. *G06T 7/0012* (2013.01); *G06T 7/0016* (2013.01); *A61B 6/037* (2013.01); *A61B 6/5217* (2013.01); *G06T 7/2053* (2013.01); *G06T 2207/10088* (2013.01); *G06T 2207/10104* (2013.01); *G06T 2207/10108* (2013.01); *G06T 2207/30016* (2013.01)

(58) Field of Classification Search
None
See application file for complete search history.

(56) References Cited

PUBLICATIONS

Merhof et al., "Analysis of Asymmetries in Ictal and Inter-Ictal SPECT Images for the Localization of Epileptic Foci";(2010) pp. 2338-2341.
Cai et al., "Special Session on Colon Liver and Brain CAD"; Springer; (2006) pp. 369-388.
McNally et al., "Localizing value of ictal-interictal SPECT analyzed by SPM (ISAS)". Epilepsia, 46(9):(2005) pp. 1450-1464.
Chang et al., "Comparison of Statistical Parametric Mapping and SPECT Difference Imaging in Patients with Temporal Lobe Epilepsy," Epilepsia, 43 (2002) pp. 68-74.
Lee et al., "Evaluation of ictal brain SPET using statistical parametric mapping in temporal lobe epilepsy,". European Journal of Nuclear Medicine, vol. 27, (2000) pp. 1658-1665.
O'Brien et al., "Subtraction ictal SPECT co-registered to MRI improves clinical usefulness of SPECT in localizing the surgical seizure focus," Neurology, vol. 50:(1998) pp. 445-454.
Zubal et al., "Difference images calculated from ictal and interictal technetium-99m-HMPAO SPECT scans of epilepsy," Journal of Nuclear Medicine, vol. 36: (1995) pp. 684-689.

*Primary Examiner* — Shervin Nakhjavan
(74) *Attorney, Agent, or Firm* — Schiff Hardin LLP

(57) ABSTRACT

In a method for localizing a candidate foci in neuroimaging, two images are acquired, one being a baseline (interictal) image and another being an intervention (ictal) image. The two images are aligned and the intensities of the images are normalized. A difference image is calculated by subtracting the baseline (interictal) image from the intervention (ictal) image. The difference image is normalized and regions of interest are selected as candidate foci.

14 Claims, 1 Drawing Sheet

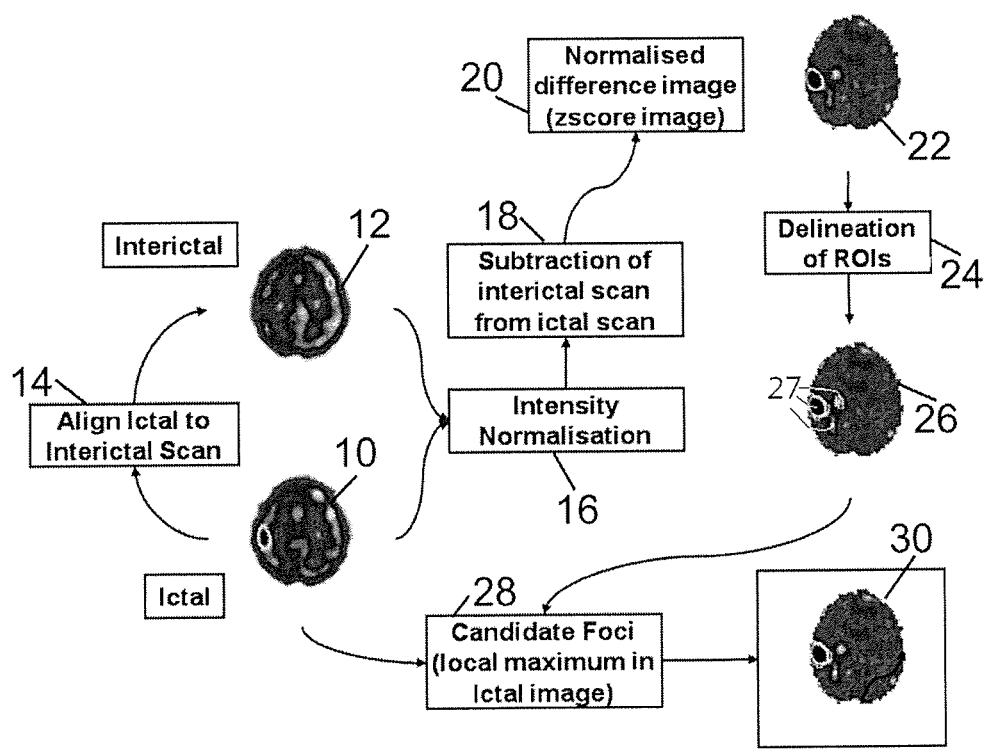

METHOD FOR LOCALIZATION OF AN EPILEPTIC FOCUS IN NEUROIMAGING

BACKGROUND OF THE INVENTION

1. Field of the Invention

The present invention concerns a method for localization of an epileptic focus in neuroimaging.

2. Description of the Prior Art

The following definitions, acronyms, and abbreviations are used herein:
ECD Ethyldysteinatdimers
HMPAO Hexamethylpropyleneamine Oxime
MRI Magnetic Resonance Imaging
PET Positron Emission Tomography
SISCOM Subtraction Ictal SPECT Co-registered to MRI
SPECT Single-Photon Emission Computed Tomography Epilepsy is a brain disorder in which a person has repeated seizures over time. Approximately 1% of the UK population is affected by epilepsy which is usually controlled (but not cured) with medication. However, 25-30% of people with epilepsy do not have seizure control even with the best available medications.

Surgery may be considered in difficult cases, where a required evaluation will include neurological examination, routine EEG, Long-term video-EEG monitoring, neuropsychological evaluation, and neuroimaging using modalities such as MRI, SPECT and PET.

Once a patient is considered for surgery, the exact location of the epileptic focus needs to be established. Functional SPECT imaging is one imaging technique that could reveal alterations in cerebral metabolism. Images captured during a seizure are referred to as "ictal" or "intervention", while those captured between seizures are referred to as "interictal" or "baseline". Ictal SPECT studies can be obtained by injecting appropriate radioisotope (99mTc-ECD or 99mTc-HMPAO) within seconds of a seizure onset to measure cerebral perfusion. Epileptic areas are hypometabolic between seizures and hypermetabolic during seizures.

One way to facilitate the localization of an epileptic focus is to subtract an interictal image from a corresponding ictal image after alignment and intensity normalization. The resulting difference image identifies areas showing significantly different ictal and interictal uptakes. The identified area may be overlaid on a corresponding MRI image to find the anatomical correspondence. This is called the Subtraction Ictal SPECT Co-registered to MRI (SISCOM) Zubal et al., "Difference images calculated from ictal and interictal technetium-99m-HMPAO SPECT scans of epilepsy," Journal of Nuclear Medicine, Vol. 36: (1995) pp. 684-689.

Accordingly, one way to facilitate the localization of an epileptic focus in SPECT imaging is to analyze a corresponding SPECT difference image. Once the intervention and baseline images (ictal and interictal images) are registered and intensity normalized, the image data are subtracted, preferably only in the area of the brain outline.

The difference image acquired in this way is beneficial in helping clinicians in identifying epileptic foci O'Brien et al. "Subtraction ictal SPECT co-registered to MRI improves clinical usefulness of SPECT in localizing the surgical seizure focus," Neurology, Vol. 50:(1998) pp 445-454. The difference image will have regions with both positive and negative variations. These variations could help in identifying areas showing significantly different uptake. However, difference images acquired according to current methods can be difficult to interpret as they may show too many potential areas of high variation, most of which are in fact irrelevant, and distracting.

Few techniques exist to facilitate the location of epileptic foci. The oldest proposes the classical SISCOM method mentioned above [Zubal1995, O'Brien1998]. To help in the analysis, the difference image is first normalized to a Z-score image, that is to say, a mean value of the image data in the region of interest is calculated. In the present context, the region of interest is the image of the brain. The calculated mean value is then subtracted across the difference image and the resulting value of each pixel divided by the standard deviation of the difference in the brain only. Then, a threshold, corresponding to a number of standard deviations, is selected to visualize and delineate potential foci of interest. However, this has often been found to identify too many potential focus areas. In the references Zubal1995 and O'Brien1998 no further processing is proposed on the difference image to facilitate its interpretation.

More recently-developed methods use ictal SPECT analysis by SPM (statistical parametric mapping), that is, by comparing ictal-interictal pairs to normal images stored in a reference database Lee et al., "Evaluation of ictal brain SPET using statistical parametric mapping in temporal lobe epilepsy,". European Journal of Nuclear Medicine, Vol. 27, (2000) pp 1658-1665 or use ictal-interictal SPECT analyzed by SPM (statistical parametric mapping), that is, by comparing ictal-interictal pairs to pairs of normal images stored in a reference database. Such techniques are described in McNally et al. "Localizing value of ictal-interictal SPECT analyzed by SPM (ISAS)," Epilepsia, 46(9):1450-64 (2005) and Chang et al. "Comparison of Statistical Parametric Mapping and SPECT Difference Imaging in Patients with Temporal Lobe Epilepsy," Epilepsia, 43:68-74 (2002).

SUMMARY OF THE INVENTION

The present invention accordingly addresses the above issues and provides improved methods for identifying candidate foci in neuroimaging by reducing the amount of distracting information with the aim to facilitate interpretation.

The above object is achieved in accordance with the present invention by a method for localizing candidate foci in neuroimaging, wherein two images are provided to a processor, the images being a baseline (interictal) image and an intervention (ictal) image. In the processor, the two images are aligned, and the respective intensities of the aligned images are normalized. A difference image is computed by subtracting the baseline image from the intervention image, and this difference image is normalized. Regions of interest are selected, and are propagated either into the intervention image or the baseline image. Regions of interest are eliminated that do not correspond to regions having a local maximum in the intervention image, or the baseline image, into which the regions of interest have been propagated. In the processor, foci regions are maintained as candidate foci, which correspond to regions that have a local maximum in the intervention region, or the baseline region, into which the regions of interest have been propagated. The candidate foci are then made available in electronic form at an output of the processor.

BRIEF DESCRIPTION OF THE DRAWINGS

The single FIGURE shows a flow chart illustrating an embodiment of the method according to the present invention.

DESCRIPTION OF THE PREFERRED EMBODIMENTS

The present invention provides a method for identifying candidate foci, in which no comparisons are made to a normal database, but the necessary information is extracted directly from an ictal-interictal difference image, itself derived as defined in the SISCOM method discussed above.

According to a method of the present invention, the process proceeds as in the conventional method described above as far as normalizing the difference image to a Z-score image and applying a threshold corresponding to number of standard deviations. By applying such a threshold, all potential focus regions in the difference image are identified.

As discussed above, this may result in identifying many potential focus regions. To reduce the amount of distracting information produced in the method so far, the present invention provides further steps in which the difference image is analyzed, and the intervention (ictal) image is compared to the analyzed difference image to confirm or reject potential clinically significant focus regions.

According to an embodiment of the present invention, all delineated regions in the difference image are propagated to the ictal image. Where a propagated region has a local maximum in the intervention (ictal) image, the propagated region is kept as a potential focus. Where a propagated region has no local maximum in the intervention (ictal) image, the propagated region is eliminated and not considered as a potential focus.

Results show that this significantly reduces the number of regions of interest that are identified as candidate foci.

The FIGURE shows a flowchart of an example method of the invention. At the start of the method, ictal 10 and interictal 12 neuroimages are acquired. An alignment step 14 is performed to align the ictal and interictal images. A conventional intensity normalization step 16 is preferably carried out, to ensure that the intensities of the ictal and interictal images are comparable.

Once intensity normalization is complete, the interictal image is subtracted from the ictal image at step 18 and a resultant difference image is produced. It may be normalized, for example using the Z-score method described above to provide a normalized Z-score image 22. In another conventional step as described above, a threshold value is set, expressed as a number of standard deviations of the range of pixel values in the normalized Z-score image 22. By applying this threshold in step 24, regions of interest 27 exceeding the defined threshold are delineated in a delineated image 26.

In a final method step 28, each of the delineated regions of interest 27 identified in the delineated image 26 is compared to the corresponding region of the ictal image 10. For each region of interest, the corresponding region of the ictal image 10 is analyzed to detect a local maximum. If a local maximum is present in the corresponding region of the ictal image 10, the region of interest 27 is confirmed as a candidate focus region, and identified as such in a final image 30. If no local maximum is present in the corresponding region of the ictal image 10, the region of interest 27 is rejected as a candidate focus region, and not identified as a candidate focus in the final image 30.

Variations of the method are possible, as will be recognized by those skilled in the art, without departing from the scope of the present invention. For example, the method of the invention may be employed with images captured using other modalities, such as PET, and/or using different tracers.

The method of the present invention may be applied for follow-up studies where there already exists a scan image for a particular patient that can be considered as a baseline, and another as an intervention scan, typically a newly-captured image.

Optionally, the baseline and intervention images may be smoothed prior to the subtraction step 18.

When the regions of interest 27 are propagated from the delineated, normalized difference image 26 to the intervention (ictal) image 10, other statistics can be used, such as mean.

In an alternative embodiment of the method of the present invention, the regions of interest 27 could be propagated to the baseline (interictal) image 12, rather than the ictal image 10, and the confirmation of candidate focus regions at step 28 may be performed by detection of whether a corresponding region of the interictal image 12 contains a local minimum.

An optional step of the method of the present invention is to modify the area of each region of interest 27 before the comparison step 28. For example, the regions of interest 27 in image 26 may be dilated, for example by one pixel before comparison 28, thus defining a larger region of the ictal 10 or interictal 12 image, within which a local maximum, or minimum, is sought.

The present invention accordingly provides a method to select candidate foci. Regions of interest 27 having high variation in the difference image 26 are propagated to the intervention (ictal) image, and if a corresponding region in the ictal image contains a local maximum then the region of interest is kept, and if not it is eliminated. Alternatively, regions of interest 27 having high variation in the difference image 26 are propagated to the baseline (interictal) image, and if a corresponding region in the interictal image contains a local minimum then the region of interest is kept, and if not it is eliminated.

The candidate foci may then be registered to a corresponding MRI scan to provide an anatomical location of the foci.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for localizing candidate foci in neuroimaging, comprising the steps of:
    providing two images to a processor, said images comprising a baseline image and an intervention image, each exhibiting image intensities;
    in said processor, aligning the two images;
    in said processor, normalizing (the intensities of the aligned images;
    in said processor, computing a difference image by subtracting the baseline image from the intervention image;
    in said processor, normalizing the difference image;
    in said processor, selecting regions of interest;
    in said processor, propagating the regions of interest to the intervention image;
    in said processor, eliminating regions of interest that do not correspond to regions having a local maximum in the intervention image; and
    in said processor, maintaining, as candidate foci, foci regions of interest that correspond to regions having a local maximum in the intervention image, and making the candidate foci available in electronic form at an output of the processor.

2. A method according to claim 1, comprising normalizing the difference image by generating a Z-score image using the mean and standard deviation of all pixels in the difference image in the brain outline, by subtracting a mean pixel value across the difference image and dividing the resulting value of each pixel by a standard deviation of the pixel data in the difference image.

3. A method according to claim 2, comprising selecting regions of interest by defining a certain threshold as a number of standard deviations of pixel intensity in the Z-score image, and selecting as regions of interest any regions of the Z-score image having pixels of intensity greater than the threshold.

4. A method according to claim 1, further comprising, in said processor, identifying said candidate foci in a final image, and making said final image available at an output of the processor in electronic form.

5. A method according to claim 1, comprising smoothing the baseline and intervention images prior to subtracting.

6. A method according to claim 1, comprising modifying the regions of interest in area before propagating.

7. A method according to claim 6, comprising dilating the regions of interest before propagating.

8. A method for localizing candidate foci in neuroimaging, comprising the steps of:
   providing two images to a processor, said images comprising a baseline image and an intervention image, each exhibiting image intensities;
   in said processor, aligning the two images;
   in said processor, normalizing (the intensities of the aligned images;
   in said processor, computing a difference image by subtracting the baseline image from the intervention image;
   in said processor, normalizing the difference image;
   in said processor, selecting regions of interest;
   in said processor, propagating the regions of interest to the baseline image;
   in said processor, eliminating regions of interest that do not correspond to regions having a local maximum in the intervention image; and
   in said processor, maintaining, as candidate foci, foci regions of interest that correspond to regions having a local maximum in the intervention image, and making the candidate foci available in electronic form at an output of the processor.

9. A method according to claim 8, comprising normalizing the difference image by generating a Z-score image using the mean and standard deviation of all pixels in the difference image in the brain outline, by subtracting a mean pixel value across the difference image and dividing the resulting value of each pixel by a standard deviation of the pixel data in the difference image.

10. A method according to claim 9, comprising selecting regions of interest by defining a certain threshold as a number of standard deviations of pixel intensity in the Z-score image, and selecting as regions of interest any regions of the Z-score image having pixels of intensity greater than the threshold.

11. A method according to claim 8, further comprising, in said processor, identifying said candidate foci in a final image, and making said final image available at an output of the processor in electronic form.

12. A method according to claim 8, comprising smoothing the baseline and intervention images prior to subtracting.

13. A method according to claim 8, comprising modifying the regions of interest in area before propagating.

14. A method according to claim 13, comprising dilating the regions of interest before propagating.

* * * * *